US 9,757,199 B2

(12) United States Patent
Chia et al.

(10) Patent No.: US 9,757,199 B2
(45) Date of Patent: Sep. 12, 2017

(54) SURGICAL LASER SYSTEMS AND LASER LITHOTRIPSY TECHNIQUES

(71) Applicant: Boston Scientific Scimed, Inc., Maple Grove, MN (US)

(72) Inventors: Wen-Jui Ray Chia, Sunnyvale, CA (US); Rongwei Jason Xuan, Fremont, CA (US); Thomas C. Hasenberg, Campbell, CA (US); Jian James Zhang, Santa Clara, CA (US); Steven Yihlih Peng, Fremont, CA (US); Danop Rajabhandharaks, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 151 days.

(21) Appl. No.: 14/387,310

(22) PCT Filed: Mar. 11, 2013

(86) PCT No.: PCT/US2013/030136
§ 371 (c)(1),
(2) Date: Sep. 23, 2014

(87) PCT Pub. No.: WO2013/154708
PCT Pub. Date: Oct. 17, 2013

(65) Prior Publication Data
US 2015/0289937 A1 Oct. 15, 2015

Related U.S. Application Data

(60) Provisional application No. 61/623,256, filed on Apr. 12, 2012, provisional application No. 61/726,713, filed on Nov. 15, 2012.

(51) Int. Cl.
*A61B 18/26* (2006.01)
*A61B 5/00* (2006.01)
(Continued)

(52) U.S. Cl.
CPC .......... *A61B 18/26* (2013.01); *A61B 1/00009* (2013.01); *A61B 1/307* (2013.01);
(Continued)

(58) Field of Classification Search
CPC ..... A61B 18/26; A61B 1/00009; A61B 1/307; A61B 2017/00061; A61B 2017/00172;
(Continued)

(56) References Cited

U.S. PATENT DOCUMENTS 5,009,658 A  4/1991 Damgaard-Iversen et al.
5,209,234 A *  5/1993 LaRocca ............ A61B 17/2256
                                                     600/439
(Continued)

FOREIGN PATENT DOCUMENTS

EP         0365754 A1    5/1990
WO      WO 90/14797     12/1990
(Continued)

OTHER PUBLICATIONS

EPO Communication pursuant to Rules 161 and 162 EPC from corresponding European Patent Application No. 13775300.0 dated Nov. 19, 2014.
(Continued)

*Primary Examiner* — Christopher A Flory
*Assistant Examiner* — Jonathan Kuo
(74) *Attorney, Agent, or Firm* — Bookoff McAndrews, PLLC

(57) ABSTRACT

A surgical laser system includes a first laser source, a second laser source, a beam combiner and a laser probe. The first laser source is configured to output a first laser pulse train comprising first laser pulses. The second laser source is configured to output a second laser pulse train comprising second laser pulses. The beam combiner is configured to combine the first and second laser pulse trains and output a
(Continued)

combined laser pulse train comprising the first and second laser pulses. The laser probe is optically coupled to an output of the beam combiner and is configured to discharge the combined laser pulse train.

20 Claims, 4 Drawing Sheets

(51) Int. Cl.
| | |
|---|---|
| A61B 1/307 | (2006.01) |
| A61B 5/20 | (2006.01) |
| A61B 1/00 | (2006.01) |
| A61B 17/00 | (2006.01) |
| A61B 18/00 | (2006.01) |
| A61B 18/20 | (2006.01) |

(52) U.S. Cl.
CPC .............. *A61B 5/0084* (2013.01); *A61B 5/20* (2013.01); *A61B 5/0051* (2013.01); *A61B 5/0075* (2013.01); *A61B 2017/00061* (2013.01); *A61B 2017/00172* (2013.01); *A61B 2018/0088* (2013.01); *A61B 2018/00511* (2013.01); *A61B 2018/00517* (2013.01); *A61B 2018/00642* (2013.01); *A61B 2018/00732* (2013.01); *A61B 2018/00982* (2013.01); *A61B 2018/207* (2013.01); *A61B 2505/05* (2013.01); *A61B 2562/223* (2013.01)

(58) Field of Classification Search
CPC  A61B 2018/00511; A61B 2018/00517; A61B 2018/00642; A61B 2018/00732; A61B 2018/0088; A61B 2018/00982; A61B 2018/207; A61B 17/22–17/22029; A61B 7/00–2007/027
USPC ..................... 606/2.5, 11, 127–128
See application file for complete search history.

(56) References Cited

U.S. PATENT DOCUMENTS

| | | | |
|---|---|---|---|
| 5,387,211 A |  | 2/1995 | Saadatmanesh et al. |
| 5,642,370 A |  | 6/1997 | Mitchell et al. |
| 5,769,840 A |  | 6/1998 | Schirmer |
| 6,004,330 A | * | 12/1999 | Middleman ............ A61B 10/02 606/127 |
| 6,358,243 B1 |  | 3/2002 | Esterowitz et al. |
| 6,413,267 B1 | * | 7/2002 | Dumoulin-White . A61N 5/0616 128/898 |
| 2006/0084957 A1 | * | 4/2006 | Delfyett ................ A61B 18/20 606/12 |
| 2008/0226029 A1 |  | 9/2008 | Weir et al. |
| 2009/0156900 A1 |  | 6/2009 | Robertson |
| 2010/0137847 A1 |  | 6/2010 | Cecchetti et al. |
| 2010/0145319 A1 |  | 6/2010 | Zimare et al. |
| 2011/0060256 A1 |  | 3/2011 | Schwarz et al. |
| 2011/0218524 A1 | * | 9/2011 | Cattaneo ................ A61B 18/22 606/12 |
| 2015/0133950 A1 | * | 5/2015 | Shelton .............. A61B 17/2202 606/128 |

FOREIGN PATENT DOCUMENTS

| | | |
|---|---|---|
| WO | 92/03977 A2 | 3/1992 |
| WO | WO 93/07806 | 4/1993 |
| WO | 2013154708 A1 | 10/2013 |

OTHER PUBLICATIONS

Examiner's Report from Canadian Intellectual Property Office for Canadian Patent Application No. 2,869,713, dated Sep. 23, 2015.
International Search Report and Written Opinion of PCT/US2013/030136, mailed May 16, 2013.
U.S. Appl. No. 61/623,256, filed Apr. 12, 2012.
U.S. Appl. No. 61/726,713, filed Nov. 15, 2012.
First Examination Report from Australian Patent Application No. 2013246481, dated Jun. 16, 2015.
Partial Supplementary European Search Report from European Patent Application No. 13775300.0, dated Sep. 17, 2015.
Examination Report dated Oct. 10, 2016, in corresponding European Patent Application No. 13775300.0-1666 (6 pages).

* cited by examiner

SURGICAL LASER SYSTEMS AND LASER LITHOTRIPSY TECHNIQUES

CROSS-REFERNCE TO RELATED APPLICATION

This Application is a Section 371 National Stage Application of International Application No. PCT/US2013/030136 filed Mar. 11, 2013 and published as WO 2013/154708 A1 on Oct. 17, 2013 in English, which claims benefit of U.S. Provisonal Application Ser. No. 61/623,256, filed Apr. 12, 2012 and U.S. Provisional Application Ser. No. 61/726,713, filed Nov. 15, 2012 under 35 U.S.C. §119(e). The contents of each of the above-identified applications are hereby incorporated by reference in the their entirety.

BACKGROUND

Embodiments of the present invention generally relate to surgical laser systems, laser pulse trains produced by such systems, and methods of performing laser lithotripsy using the systems and laser pulse trains.

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy as part of the treatment protocol.

The treatment of kidney or bladder calculi or stones, Lithotripsy, is currently achieved through either ESWL (extra-corporal sound wave lithotripsy), surgery, or use of a laser (laser lithotripsy). In the laser application, a holmium doped yttrium aluminium garnet (Ho:YAG) laser rod, or a thulium doped yttrium aluminium garnet (Tm:YAG) laser rod are used to produce laser energy having a wavelength of around 2000-2100 nm to break up stones of all types. The laser energy is typically in the form of a train of laser pulses, each having long pulse widths, such as approximately a few hundred microseconds. It is believed that a thermo-mechanical mechanism of action is in play for breaking up the stones, namely the laser energy superheats water in the vicinity of the stone, and creates a vaporization bubble. The vaporization bubble then expands and destabilizes the stone, causing it to fragment.

There is a continuous demand for improvements to laser lithotripsy procedures including improved fragmentation of the stones, for example.

SUMMARY

Figure 1:
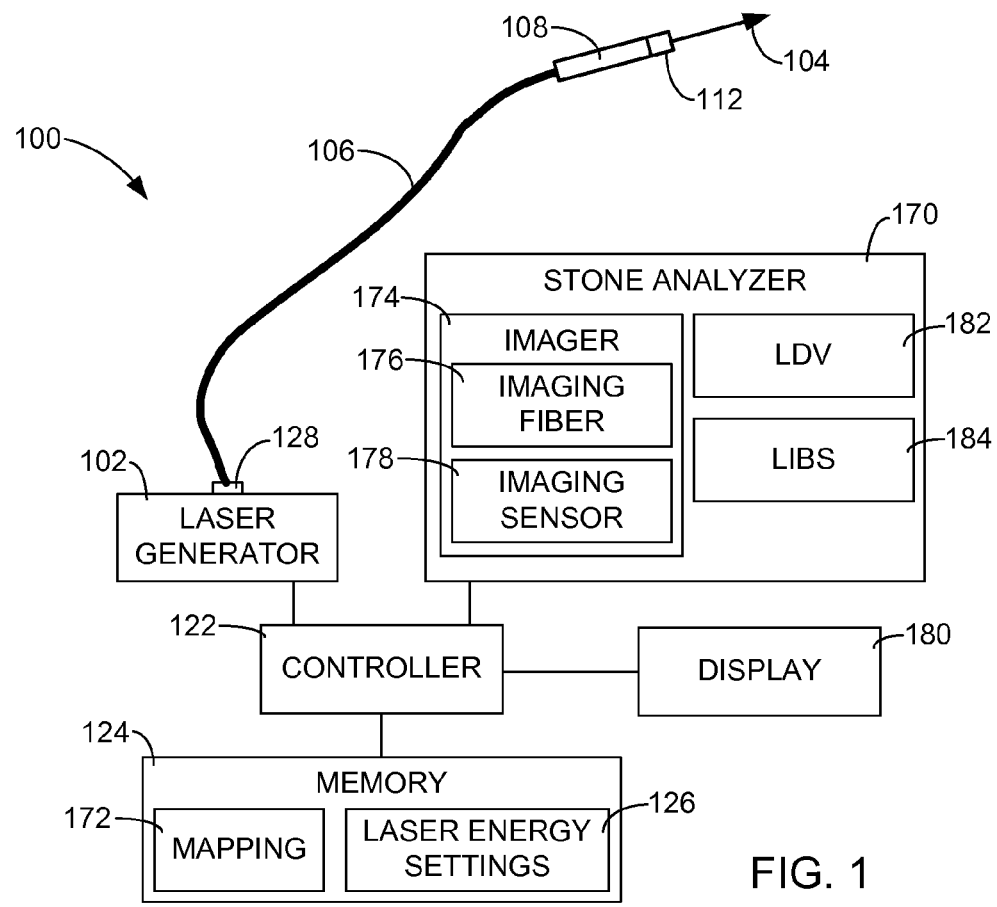
FIG. 1 is a schematic diagram of an exemplary surgical laser system in accordance with embodiments of the invention.

Embodiments of the invention generally relate to surgical laser systems, laser pulse trains produced by such systems, and methods of performing laser lithotripsy procedures using the systems and the laser pulse trains In some embodiments, a surgical laser system (100) includes a first laser source (140A), a second laser source (140B), a beam combiner (142) and a laser probe (108). The first laser source is configured to output a first laser pulse train (144, 104A) comprising first laser pulses (146). The second laser source is configured to output a second laser pulse train (148, 104B) comprising second laser pulses (150). The beam combiner is configured to combine the first and second laser pulse trains and output a combined laser pulse train (152, 104) comprising the first and second laser pulses. The laser probe is optically coupled to an output of the beam combiner and is configured to discharge the combined laser pulse train.

In some embodiments, the first laser pulses are temporally offset from the second laser pulses in the combined laser pulse train. In some embodiments, the first laser pulses alternate with the second laser pulses in the combined laser pulse train. In some embodiments, a pulse width (134) of the first laser pulses and the second laser pulses is in the range of 0.1-10,000 ns, 1 ns-500 μs, or 1 ps-10 ms. In some embodiments, the combined laser pulse train has a pulse repetition rate in the range of 1 Hz-2 GHz, or 0.1 Hz-10 GHz. In some embodiments, the first laser pulses each have a first wavelength, the second laser pulses each have a second wavelength, and the first and second wavelengths are different. In some embodiments, the system includes a delay generator (154) configured to delay discharge of the second laser pulse train (148) from the second laser source (140B) relative to the discharge of the first laser pulse train (144) from the first laser source (140A).

In some embodiments, a surgical laser system includes a laser generator (102), a laser probe (108), a stone analyzer (170), and a controller (122). The laser generator is configured to generate laser energy (104) based on laser energy settings (126). The laser probe is configured to discharge the laser energy. The stone analyzer has an output relating to a characteristic of a targeted stone (120). The controller comprises at least one processor configured to determine the laser energy settings based on the output.

In some embodiments, the laser energy comprises a train (130) of laser pulses (132), and the laser energy settings include settings for a pulse width of the laser pulses, a pulse repetition rate of the laser pulses, a power of the laser pulses, a wavelength of the laser pulses, and/or a duration of the train of the laser pulses. In some embodiments, the system includes memory (124) comprising a mapping (172) of laser energy settings to values of the output, wherein the controller controls the laser generator based on the laser energy settings of the mapping corresponding to the output. In some embodiments, the characteristic is an estimated size of the stone, an estimated length of the stone, an estimated composition of the stone and/or a vibration frequency of the stone. In some embodiments, the output from the stone analyzer is an image of the stone, a laser induced vibration measurement of the stone, and/or a spectrometer reading of the stone. In some embodiments, the stone analyzer comprises an imager (174) configured to output an image of the targeted stone, and the controller is configured to estimate a length of at least one dimension of the stone based on the image, and control the laser generator based on the laser energy settings corresponding to the length estimate in the mapping. In some embodiments, the stone analyzer comprises a Laser Doppler Vibrometer (182) configured to measure a vibration frequency of the targeted stone, and the controller is configured to control the laser generator based on the laser energy settings corresponding to the measured vibration frequency in the mapping. In some embodiments, the stone analyzer comprises a laser induced breakdown spectrometer (184) configured to output a spectrometer reading indicative of a composition of the targeted stone, and the controller is configured to control the laser generator based on the laser energy settings corresponding to the spectrometer reading in the mapping.

In some embodiments of a method of fragmenting a targeted kidney or bladder stone, a first laser pulse train (144) comprising first laser pulses (146) is generated using a first laser source (140A). A second laser pulse train (148) comprising second laser pulses (150) is generated using a second laser source (140B). The first and second laser pulse trains are combined into a combined laser pulse train (152) comprising the first and second laser pulses. The stone is exposed to the combined laser pulse train using a laser probe (108). The stone is fragmented in response to exposing the stone to the combined laser pulse train.

In some embodiments of the method, the first and second laser pulse trains are combined such that the first laser pulses are temporally offset from the second laser pulses. In some embodiments, the first laser pulses are temporally offset from the second laser pulses by delaying the generation of the second laser pulse train relative to the generation of the first laser pulse train.

In some embodiments of a method of fragmenting a targeted kidney or bladder stone, an output relating to a characteristic of the targeted stone (120) is generated using a stone analyzer (170). Embodiments of the characteristic include an estimated size of the stone, an estimated length of the stone, an estimated composition of the stone, and a vibration frequency measurement of the stone. Laser energy settings (126) are generated based on the output. Laser energy (104) is generated using a laser generator in accordance with the laser energy settings. The stone is exposed to the laser energy using a laser probe (108). The stone is fragmented in response to exposing the stone to the laser energy.

In some embodiments, the laser energy comprises a train (130) of laser pulses (132). In some embodiments, the laser energy settings include settings of a pulse width of the laser pulses, a pulse repetition rate of the laser pulses, a power of the laser pulses, a wavelength of the laser pulses, and/or a duration of the train of the laser pulses.

In some embodiments of a method of fragmenting a targeted kidney or bladder stone (120), the stone is exposed to first laser energy (130) having a first power level using a laser probe (108). The stone is exposed to second laser energy (164) having a second power level using the laser probe, wherein the second power level is higher than the first power level. The stone is fragmented in response to exposing the stone to the second laser energy.

In some embodiments, the stone is exposed to the second laser energy after exposing the stone to the first laser energy. In some embodiments, the stone is exposed to the second laser energy after the exposure of the stone to the first laser energy begins. In some embodiments, the first laser energy comprises a laser pulse train (130) having a pulse repetition rate in the range of approximately 1 kHz-2 GHz. In some embodiments, the second laser energy comprises a single laser pulse (164). In some embodiments, the second laser energy comprises a laser pulse train.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Embodiments of the present invention generally relate to surgical laser systems, laser pulse trains produced by such systems, and methods of performing laser lithotripsy procedures using the systems and the laser pulse trains. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium referred to herein as "memory" may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Figure 2:
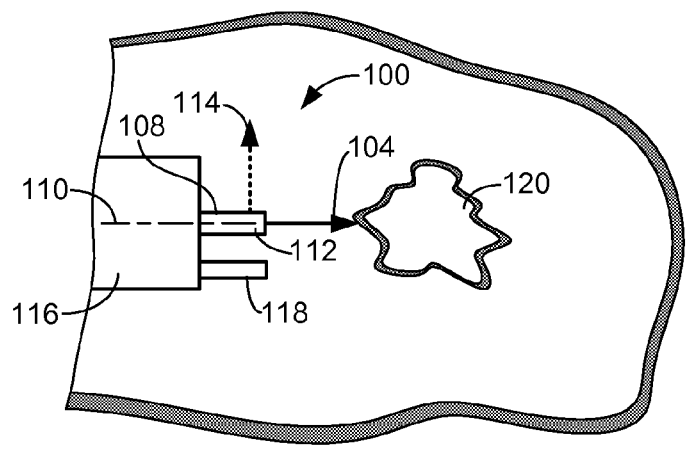
FIG. 2 is a simplified illustration of an exemplary laser lithotripsy procedure in accordance with embodiments of the invention.

FIG. 1 is a schematic diagram of an exemplary surgical laser system 100, and FIG. 2 is a simplified illustration of an exemplary laser lithotripsy procedure on a stone using the system 100, in accordance with embodiments of the invention. In some embodiments, the system 100 comprises a laser generator 102 that generates laser energy 104. In some embodiments, the laser energy 104 is optically coupled to a waveguide 106, such as an optical fiber, and discharged from a laser probe 108 to perform a desired procedure, such as tissue ablation or urinary or kidney stone fragmentation.

In some embodiments, the laser generator 102 comprises one or more conventional laser sources, such as laser resonators, that produce the laser energy 104 having desired properties. In some embodiments, the system 100 produces the laser energy 104 in the form of a pulse train comprising pulses having a relatively short pulse width and at a relatively high pulse repetition rate, as compared to laser systems of the prior art, particularly those used in laser lithotripsy procedures. In some embodiments, the laser generator 102 includes Q-switched laser rods to produce the laser energy 104, such as, for example, a holmium doped yttrium aluminium garnet (Ho:YAG) laser rod, a thulium doped yttrium aluminium garnet (Tm:YAG) laser rod, or other conventional laser rod suitable for producing the desired laser energy 104.

The laser probe 108 may be configured to discharge the laser energy 104 along a longitudinal axis 110 of the probe through a distal end 112, as shown in FIG. 2, laterally relative to the longitudinal axis of the probe 108 (side-fire laser probe), as indicated by the arrow 114, or discharge the laser energy 104 in another conventional manner. The laser probe 108 may be supported in a cystoscope or endoscope 116, a distal end of which is illustrated in FIG. 2.

In some embodiments, the system 100 includes a secondary probe 118, a distal end of which is illustrated in FIG. 2. The secondary probe 118 may be used, for example, to capture images of a targeted stone 120, or perform other functions. In some embodiments, the probe 118 may be used to obtain one or more characteristics of the targeted stone 120, as discussed below.

In one embodiment, the system 100 includes a controller 122 that includes one or more processors that are configured to execute program instructions stored in memory 124, or other location, to carry out various functions described herein. In some embodiments, the controller 122 controls the laser generator 102 in accordance with laser energy settings 126 stored in the memory 124, or other location.

In some embodiments, the controller 122 controls the discharge of the laser energy 104 through the laser probe 108 using conventional techniques. For instance, the controller 122 may control one or more shutter mechanisms 128 (FIG. 1), which may control the discharge of the laser energy 104 to the waveguide 106, or the discharge of laser energy from individual laser sources of the laser generator 102.

Figure 3:
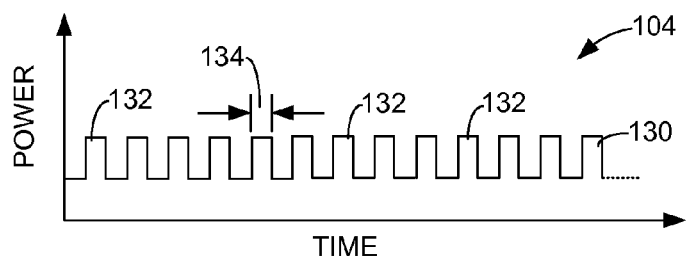
FIG. 3 is a chart illustrating an exemplary laser pulse train in accordance with embodiments of the invention.

In some embodiments, the system 100 is configured to generate laser energy 104 in the form of a laser pulse train 130, such as the exemplary laser pulse train illustrated in FIG. 3. The laser pulse train 130 comprises individual laser pulses 132. In some embodiments, the laser pulses 132 each have a short pulse width 134 relative to the laser energy used for conventional laser lithotripsy procedures, which typically has a pulse width on the order of hundreds of microseconds. In some embodiments, the pulse width 134 of each of the pulses 132 in the train 130 is less than 1 µs, or less than 1 ms, for example. In some embodiments, the pulse width 134 is in the range of 1-10,000 ns, 0.1-500 µs, or 1 ps-10 ms, for example. Such pulse widths may be obtained using conventional Q-switched laser rods, such as those mentioned above, or other suitable technique.

In some embodiments, the laser pulses 132 are repeated at a high rate relative to conventional laser systems. In some embodiments, the pulse repetition rate is in the range of 0.001 to 1000 kHz, 1 kHz-2 GHz, greater than 1 GHz, 0.1 Hz-10 GHz. The high pulse repetition rate (GHz range) covers the life span of plasma clouds, which can enhance the laser plasma effect to achieve efficient tissue ablation or stone fragmentation.

In some embodiments, the laser generator 102 utilizes multiple laser sources to generate the high pulse repetition rate of the pulse train 130. In some embodiments, each of the laser sources is capable of producing laser energy that can cause thermal-confined or stress-confined interaction on tissue or a kidney or bladder stone. The laser energy or laser pulse trains generated by each of the two or more laser sources are combined to form the laser energy 104 having the desired high pulse repetition rate. The laser energy 104 is then discharged to the targeted object or tissue, such as a kidney or bladder stone 120 through the probe 104.

Figure 4:
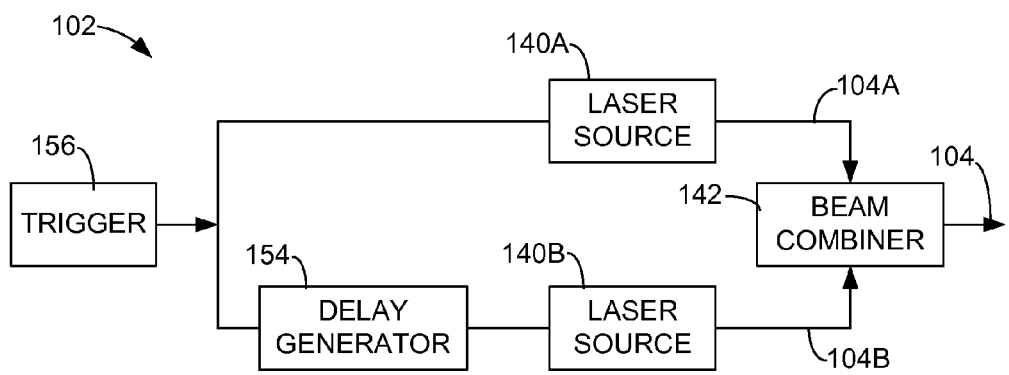
FIG. 4 is a schematic diagram of a laser generator in accordance with embodiments of the invention.

FIG. 4 is a schematic diagram of an exemplary configuration of the laser generator 102 that is configured to generate the laser energy 104 having a high pulse repetition rate. In some embodiments, the laser generator comprises a laser source 140A configured to output laser energy 104A, and a laser source 140B configured to output laser energy 104B. In some embodiments, the laser sources may be Q-switched laser sources or other conventional devices capable of generating the laser energies 104A and 104B each having a pulse width and a pulse repetition rate that is set in accordance with the laser energy settings 126.

In some embodiments, a beam combiner 142 combines the laser energies 104A and 104B, such that they overlap into a single laser beam as the laser energy 104. In some embodiments, the beam combiner 142 comprises conventional minors, lenses and/or other optical components to combine the laser pulse energies 104A and 104B. More than two laser sources may also be combined in this manner to produce pulse trains having high pulse repetition rates. The output laser energy 104 from the beam combiner 142 is optically coupled to the laser probe 108 for discharge, as shown in FIG. 1.

Figure 5:
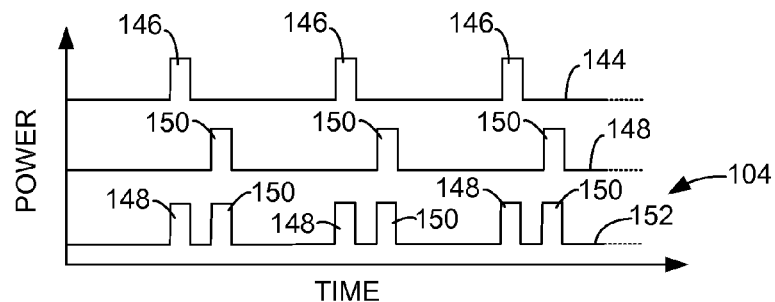
FIGS. 5 and 6 are charts illustrating exemplary laser pulse trains in accordance with embodiments of the invention.

In one embodiment, the laser energy 104A comprises a laser pulse train 144 of laser pulses 146, and the laser energy 104B comprises a laser pulse train 148 of laser pulses 150, as illustrated in the chart of FIG. 5. In some embodiments, the pulses 146 and 150 may be of the same or different wavelength, the same or different pulse width, and the same or different pulse shape. In some embodiments the laser pulse trains 144 and 148 may have a pulse repetition rate or frequency that is the same or different. In accordance with some embodiments, the pulses 146 and 150 have a wavelength in the range of 400-11000 nm, 300-20000 nm. In some embodiments, the pulses 146 and 150 have a pulse width in the range of, less than 1 µs, 0.1-10000 ns, or 1 ps-10 ms, for example. In some embodiments, the pulse trains 144 and 148 have a pulse repetition rate in the range of 0.1 z-10 GHz.

In some embodiments, the pulses 146 of the pulse train 144 are temporally offset from the pulses 150 of the pulse train 148 to generate the pulse train 152 that forms the laser energy 104, as illustrated in FIG. 5. In some embodiments, the pulses 146 and 150 of the pulse train 152 do not overlap, as shown in FIG. 5. In some embodiments, the pulses 146 alternate with the pulses 150, as shown in FIG. 5.

The laser pulse trains produced by the two or more laser sources of the laser generator 102 may be temporally offset in any suitable manner. In one exemplary embodiment, an adjustable delay generator 154 delays the discharge of the laser pulse train 148 from the laser source 140B in response to a trigger 156 received from, for example, the controller 122 (FIG. 1). The delay of the triggering of the pulses 150 can be as small as a few nanoseconds. The trigger signal and the delayed signal may be used to control shutter mechanisms corresponding to the laser sources 140A and 140B, for example.

The resultant pulse repetition rate of the pulse train 152 of the laser energy 104 that can be achieved using the multiple laser sources is substantially higher than what would be possible using a single laser source. That is, the laser generator 102 effectively multiplies the pulse repetition rate of a conventional laser source by combining the output laser energies of two or more laser sources. Accordingly, this technique may be used to produce very high frequency pulse trains 152 for the laser energy 104, such as pulse trains having a pulse repetition rate in the range of up to 2 GHz or more, depending on the width of the pulses (e.g., 146 and 148). As discussed below, this frequency range enables the system 100 to match the high estimated natural or resonance frequencies of urinary or kidney stones to enable more thorough fragmentation of the stones during laser lithotripsy procedures.

In some embodiments, the laser pulses 146 and 150 of the laser trains 144 and 146 are not temporally offset, but directly overlap (i.e., pulses are synchronized). This allows for the generation of laser energy 104 having a higher power than would otherwise be possible using a single laser source. In some embodiments, the generator 102 is configured as described with reference to FIG. 5, but without the delay generator 154.

Figure 6:
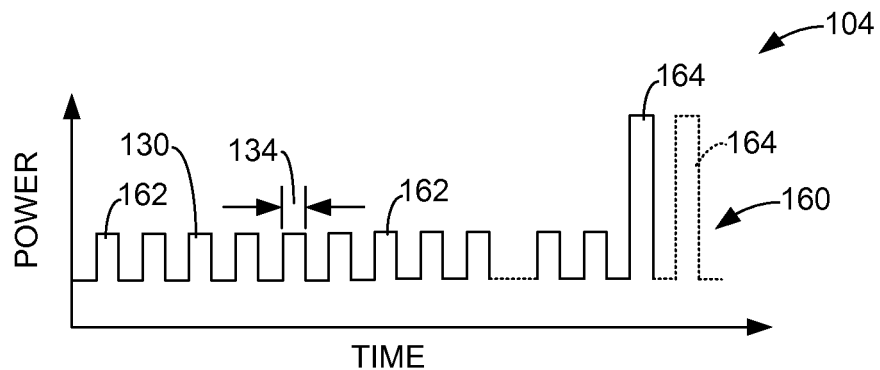

In accordance with another embodiment, the laser generator generates laser energy 104 in the form of a pulse train 160 shown in FIG. 6, which is discharged to a targeted stone 120 through, for example, the laser probe 108. In some embodiments, the pulse train 160 comprises a series of pulses 162 at a first power or energy level followed by one or more pulses 164 at a second energy level that is higher than the first energy level. In some embodiments, the pulses 162 comprise the pulses 146 and 150 and form the pulse train 130 in accordance with one or more embodiments described above. Thus, in some embodiments, the laser pulses 162 may be generated using two or more laser sources of the generator 102. Exposure of the targeted stone 120 to the pulses 162 heats the targeted stone 120 and/or produces cracks in the targeted stone 120, while the high energy pulse or pulses 164 pulverize the stone 120.

The pulses 162 and 164 may have the same or different wavelength, pulse width or pulse shape. In some embodiments, the pulses 162 have a pulse width 134 of approximately less than 1 µs, 1-10000 ns, 1 ps-10 ms. In some embodiments, the pulses 162 have an energy level of approximately 0.01-1000 mJ, 1 nJ-10 J. The pulses 162 are preferably delivered at a pulse repetition rate or frequency in the range of 1-20000 kHz, 1 kHz-2 GHz, or 0.1 Hz-10 GHz.

In some embodiments, the one or more pulses 164 have an energy level in the range of 1-10000 mJ, 1 nJ-10 J. In some embodiments, the one or more pulses 164 have a pulse width in the range of less than 1 µs, 1 ns-500 µs, 1 ps-10 ms. In some embodiments, the one or more laser pulses 164 are generated by a laser source of the laser generator 102 that is not used to generate the laser pulses 162.

In some embodiments, when a train of the laser pulses 164 is used, the train of pulses 164 has a lower frequency or pulse repetition rate than the train of pulse 162, such as 0.1 Hz-10 GHz. In some embodiments, the laser pulses 164 have a pulse repetition rate that is tuned to the stone 120 targeted for fragmentation, as described below. In some embodiments, the train of pulses 164 has a pulse repetition rate in the range of 1 kHz-2 GHz, 0.1 Hz-10 GH. In some embodiments, the train of pulses 164 is formed using a multiple laser source technique in accordance with one or more embodiments described above with regard to the laser pulse train 130.

In some embodiments, the one or more high energy laser pulses 164 occur immediately after the pulse train of lower energy laser pulses 162. In some embodiments, the generation of the one or more high energy laser pulses 164 by the generator 102 begins after the targeted stone 120 is exposed to the laser pulses 162, allowing for the one or more laser pulses 164 to overlap the laser pulses 162.

Some embodiments of the invention are directed to methods of producing the laser energy 104 using the system 100 described above, and laser lithotripsy methods for fragmenting a kidney or bladder stone using embodiments of the system. In some embodiments, the laser generator 102 is configured to output laser energy 104 in accordance with one or more embodiments described above to fragment a targeted stone 120, such as that illustrated in FIG. 2.

In some embodiments, the laser energy 104 output from the laser generator 102 is defined by laser energy settings 126 stored, for example, in the memory 124 (FIG. 1) or other location. The laser energy settings 126 may determine the wavelength of the laser energy 104, the pulse width 134 of the pulses that form the laser energy 104, the pulse repetition rate of the laser energy 104, the energy level of the pulses of the laser energy 104, the duration that the laser energy 104 is output (i.e., the duration of the laser treatment), and/or other properties of the laser energy 104 output from the laser generator 102. In some embodiments, the controller 122 uses the laser energy settings 126 to control the laser generator 102 and its one or more laser sources (e.g., laser sources 140A and 140B) to generate the laser energy 104.

In some embodiments, the laser generator 102 is configured to output laser energy 104 that is tuned to fragment the targeted stone 120. In some embodiments, this tuning of the laser energy 104 matches the frequency or the pulse repetition rate of the laser energy 104 to a natural or resonant frequency of the targeted stone 120. In some embodiments, this tuning of the laser energy 104 to the targeted stone 120 enables the laser energy 104 to more efficiently fragment the stone 120, and fragment the stone into smaller particles, than is possible using prior art laser lithotripsy techniques.

In some embodiments, the natural frequency of the targeted stone 120 can be estimated based on characteristics of the targeted stone 120. In some embodiments, the system 100 includes a stone analyzer 170 that is configured to determine, or assist in determining, one or more characteristics of the stone 120, from which a natural frequency of the stone 120 can be estimated and used to determine the laser energy settings 126. Exemplary stone characteristics include one or more dimensions of the stone, a geometry of the stone, a vibration frequency of the stone, a composition of the stone, a type of the stone, color or tensile strength, and other characteristics.

In some embodiments, the system 100 includes a mapping or look-up table 172 stored in the memory 124 (FIG. 1), or other location that is accessible by the controller 122. The mapping 172 identifies laser energy settings for various measured or estimated characteristics of the stone 120. After the controller 122 determines one or more characteristics of the targeted stone 120 using the stone analyzer 170, the controller 122 obtains the laser energy settings corresponding to the one or more determined characteristics using the mapping 172. The controller 122 then sets the laser generator 102, or the individual laser sources, to generate the laser energy 104 tuned to the stone 120 based on the settings. In some embodiments, the laser settings obtained from the mapping 172 are stored as the laser settings 126. The system 100 may then perform a laser lithotripsy procedure on the targeted stone 120 using tuned laser energy 104 to fragment the stone, as illustrated in FIG. 2.

In some embodiments, the stone analyzer 170 comprises an imager 174 configured to capture images of the targeted stone 120, as shown in FIG. 1. The imager 174 may be a conventional imaging component that comprises the secondary probe 118 (FIG. 2) in the form of an imaging fiber 176, and an imaging sensor or chip 178, such as a CCD sensor. In some embodiments, the controller 122 processes images from the imager 174 to determine characteristics of a targeted stone 120, such as a measurement or estimate of the one or more dimensions of the stone 120 (i.e., a length such as diameter, area, etc.), the stone's geometry, or other characteristic of the targeted stone 120, for example. In some embodiments, the system 100 includes a display 180 (FIG. 1) on which the images captured by the imaging sensor 178 may be displayed. In some embodiments, the one or more image-determined characteristics of the stone 120 are mapped in the mapping 172 to laser energy settings (e.g., a pulse repetition rate, pulse width, etc.) for generating laser energy 104 tuned to fragment the targeted stone 120.

In some embodiments, the stone analyzer 170 comprises a Laser Doppler Vibrometer (LDV) 182, which is an instrument used to make non-contact vibration measurements of a surface. In some embodiments, the LDV 182 exposes the stone 120 to a laser beam, such as the laser energy 104 from the laser probe 108, or a laser beam from the secondary probe 118 (FIG. 2). A vibration amplitude and frequency of the stone 120 are extracted from the Doppler shift of the frequency of the laser beam reflected from the surface of the stone 120 in response to the motion of the stone surface caused by the laser beam. This may be obtained, for example, through the imager 174, or other conventional component. The output of the LDV 182 may be a continuous analog voltage that is directly proportional to the velocity component of the stone surface along the direction of the laser beam. In some embodiments, the controller 122 determines the one or more stone characteristics, such as a vibration frequency of the stone 120, based on the output from the LDV 182. In some embodiments, one or more of these characteristics are mapped in the mapping 172 to laser energy settings, such as a pulse repetition rate, for generating laser energy 104 tuned to fragment the stone 120.

In some embodiments, the stone analyzer 170 comprises a Laser Induced Breakdown Spectrometer (LIBS) 184 configured to perform laser induced breakdown spectroscopy on a targeted stone 120 through, for example, the secondary probe 118, and output a spectrometer reading indicative of a composition of the targeted stone 120. In some embodiments, a strong plasma effect is generated using the laser energy 104, such as the high frequency pulse train 130 described above. This plasma effect is used by the LIBS 184 to obtain the composition of the stone 120. In some embodiments, the output composition of the targeted stone 120 is used to identify a type of the targeted stone 120, a natural frequency (i.e., vibration frequency) for the stone 120, and/or other characteristics of the stone 120. In some embodiments, the controller 122 determines the laser treatment to be performed to fragment the stone 120 based on the identified type of stone. In some embodiments, one or more of these characteristics are mapped in the mapping 172 to laser energy settings, such as a pulse repetition rate, for generating laser energy 104 tuned to fragment the stone 120. In some embodiments, the results of the laser induced breakdown spectroscopy on the targeted stone 120 are also used for diagnosis, treatment and recurrence prevention.

Figure 7:
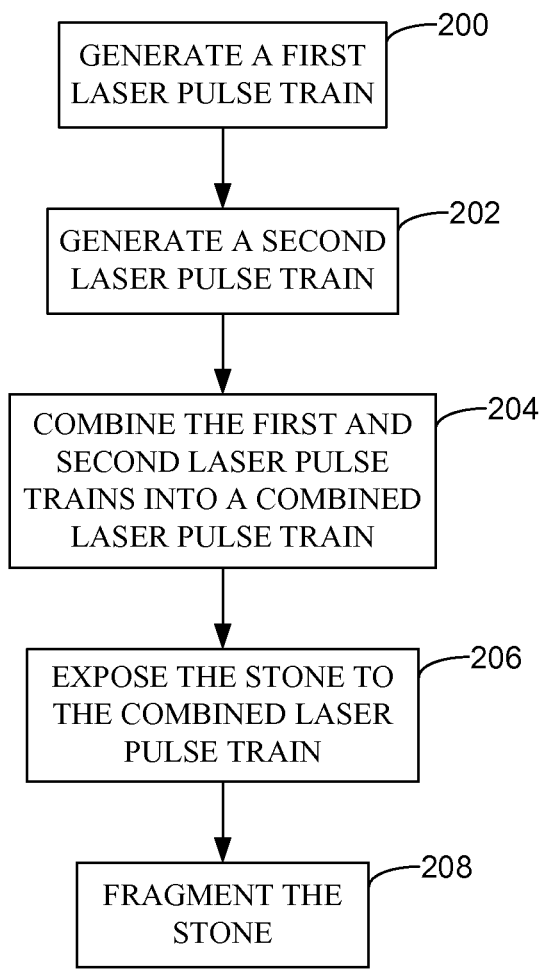
FIGS. 7-9 are flowcharts illustrating methods of fragmenting a kidney or bladder stone in accordance with embodiments of the invention.

Additional embodiments are directed to the use of the system 100 formed in accordance with one or more embodiments described herein to perform a laser lithotripsy treatment to fragment a kidney or bladder stone. FIG. 7 is a flowchart illustrating a method of fragmenting a targeted kidney or bladder stone in accordance with embodiments of the invention. At 200, a first laser pulse train, such as pulse train 144 (i.e. laser energy 104A), comprising first laser pulses 146 is generated using a first laser source 140A, as shown in FIGS. 4 and 5. At 202, a second laser pulse train 148 (i.e., laser energy 104B) comprising second laser pulses 150 is generated using a second laser source 140B. The first and second laser pulse trains 144 and 148 are combined into a combined laser pulse train 152 (i.e., laser energy 104) at 204. The combined laser pulse train 152 includes the first and second laser pulses 146 and 150. At 206, the stone 120 is exposed to the combined laser pulse train 152 using a laser probe 108, such as illustrated in FIG. 2. At 208, the stone 120 is fragmented in response to the exposure of the stone 120 to the combined laser pulse train 152.

In some embodiments, step 204 involves temporally offsetting the first laser pulses 146 from the second laser pulses 150 to form the combined laser pulse train 152 (FIG. 5) or pulse train 130 (FIGS. 3 and 6). In some embodiments, the first laser pulse train 144, the second laser pulse train 148, and the combined laser pulse train 152 are formed using the laser generator 102 described above with reference to FIG. 4. In some embodiments, the laser generator 102 comprises a delay generator 154 that delays the generation of the second laser pulse train 148 relative to the generation of the first laser pulse train 144 to temporally offset the first laser pulses 146 from the second laser pulses 150.

In some embodiments, the pulse width 134 of the first and second laser pulses 146 and 150 is in accordance with one or more embodiments described above. In some embodiments, the combined laser pulse train 152 has a pulse repetition rate in accordance with one or more embodiments described above. In some embodiments, the first and second laser pulses 146 and 150 have the same wavelength. In some embodiments, the wavelength of the first laser pulses 146 is different from the wavelength of the second laser pulses 150. In some embodiments, the wavelengths of the first and second laser pulses 146 and 150 are in accordance with one or more embodiments described above.

In accordance with another embodiment, the laser energy 104 is in the form of a pulse train, such as pulse train 152 (FIG. 5) or the pulse train 130 (FIGS. 3 and 6), having pulses (e.g., 132, 162) that are at a first power or energy level and at a high repetition rate. In some embodiments, these laser pulses are configured to heat and potentially crack the targeted stone 120. In some embodiments, the series of laser pulses of the combined laser pulse train 152 or 130 are followed by one or more high energy pulses 164 (FIG. 6) having a higher energy level than the first and second laser pulses, as shown in FIG. 6. In some embodiments of the method, the targeted stone 120 is exposed to the one or more high energy pulses 164 to pulverize the stone 120. The energy levels of the first and second laser pulses 146 and 150, or pulses 162, and the high energy pulses 164 may be in accordance with one or more of the embodiments described above.

Figure 8:
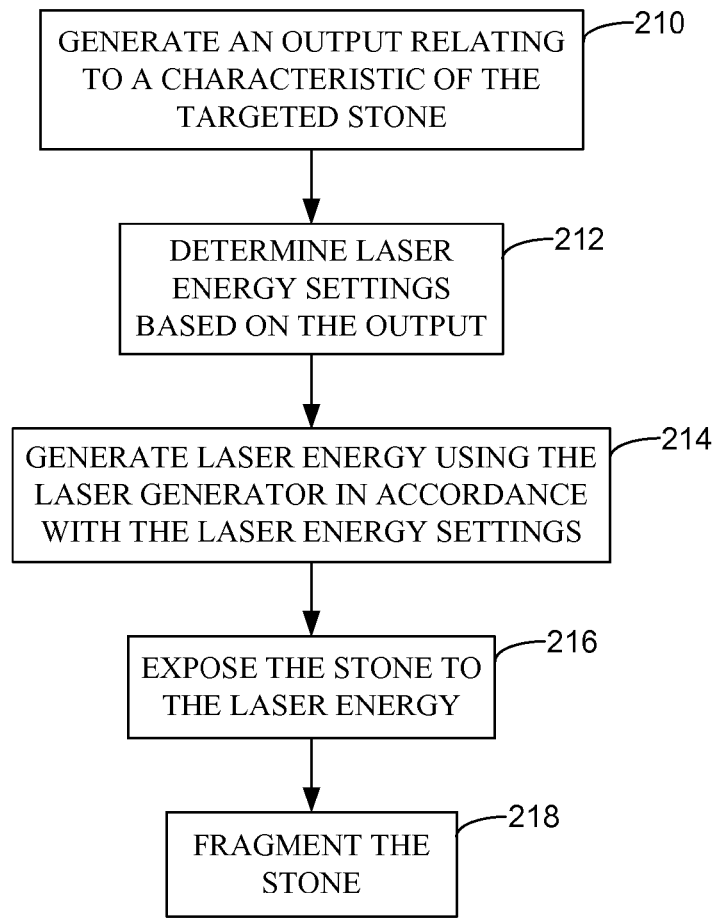

FIG. 8 is a flowchart illustrating a method of fragmenting a targeted kidney or bladder stone 120 using laser energy 104 that is tuned to the targeted stone 120. At 210, an output relating to a characteristic of the targeted stone 120 is generated. In some embodiments, the output is generated using a stone analyzer 170 in accordance with one or more embodiments described above. Exemplary embodiments of the characteristic include an estimated size of the stone, an estimated length of a dimension of the stone (i.e., a diameter of the stone), an estimated composition of the stone, a vibration frequency of the stone, and type of the stone. In some embodiments, the output relating to a characteristic of the targeted stone 120 is processed by the controller 122 to determine the characteristic of the stone 120.

At 212, laser energy settings are determined based on the output. In some embodiments, values of the output or the corresponding characteristics are mapped to laser energy settings in a mapping 172 stored in the memory of the system (FIG. 1), or other location. In some embodiments, the controller 122 uses the mapping 172 to determine the laser energy settings based on the output.

At 214, laser energy 104 is generated using a laser generator 102 in accordance with the laser energy settings. Embodiments of the laser generator 102 and the laser energy 104 include one or more embodiments described above. At 216, the targeted stone 120 is exposed to the laser energy 104 and the stone 120 is fragmented at 218 in response to the exposure.

Figure 9:
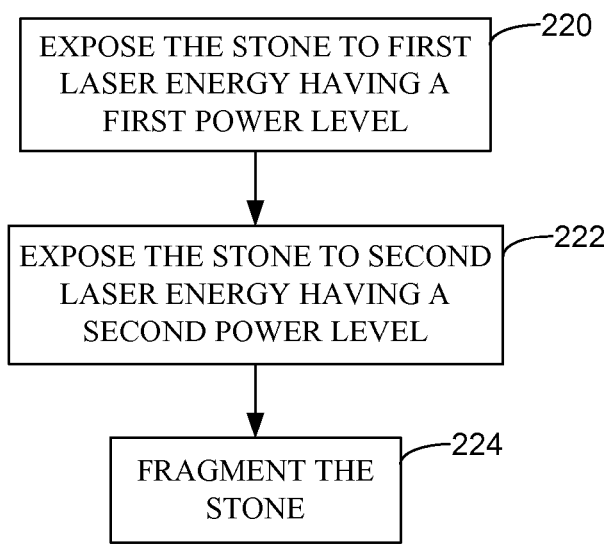

FIG. 9 is a flowchart illustrating a method of fragmenting a targeted kidney or bladder stone in accordance with embodiments of the invention. At 220, the targeted stone 120 is exposed to first laser energy (laser pulses 162 or pulse train 130) having a first power or energy level. At 222, the targeted stone 120 is exposed to second laser energy (one or more pulses 164) having a second power level. At 224, the stone 120 is fragmented in response to the exposure to the first and second laser energy. In some embodiments, the second power level is greater than the first power level, as shown in FIG. 6. For instance, the first laser energy may comprise a laser pulse train 130 comprising pulses 162 having a pulse width and a pulse repetition rate in accordance with embodiments described above with reference to FIG. 6. For instance, in some embodiments, the first laser energy comprises a laser pulse train 130 having a pulse repetition rate in the range of 1 kHz-2 GHz. In some embodiments, the first laser energy heats the targeted stone 120 and/or facilitates the generation of cracks in the targeted stone 120. In some embodiments, the second laser energy comprises one or more laser pulses 164 in accordance with one or more of the embodiments described above. The second laser energy is generally used to pulverize the targeted stone 120 after the targeted stone 120 has been weakened due to its exposure to the first laser energy.

In some embodiments, step 222 occurs after step 220, as shown in FIG. 6. In some embodiments, step 222 begins after step 220 begins. Here, there may be some overlap between steps 222 and 220.

Although the present invention has been described with reference to preferred embodiments, workers skilled in the art will recognize that changes may be made in form and detail without departing from the spirit and scope of the invention.

What is claimed is:

1. A system comprising:
 a first laser source with a first shutter mechanism configured to output a first laser pulse train comprising first laser pulses;
 a second laser source with a second shutter mechanism configured to output a second laser pulse train comprising second laser pulses;
 a beam combiner configured to combine the first and second laser pulse trains and, based on a laser energy setting, output a combined laser pulse train comprising the first and second laser pulses at a resultant pulse repetition rate;
 a laser probe optically coupled to an output of the beam combiner and configured to discharge the combined laser pulse train toward a kidney or bladder stone;
 a stone analyzer configured to receive a portion of the combined laser pulse train reflected from the stone, and generate an output relating to a characteristic of the stone, the characteristic including a natural or resonance frequency of the stone; and a controller comprising at least one processor configured to receive the output generated by the stone analyzer, and determine the laser energy setting by matching the resultant pulse repetition rate of the combined laser pulse train with the natural or resonance frequency of the stone.

2. The system of claim 1, wherein the first laser pulses are temporally offset from the second laser pulses in the combined laser pulse train.

3. The system of claim 1, wherein:
the first laser pulses each have a first wavelength;
the second laser pulses each have a second wavelength; and
the first and second wavelengths are different.

4. The system of claim 1, further comprising a delay generator operable with the first and second shutter mechanisms to delay discharge of the second laser pulse train from the second laser source relative to the discharge of the first laser pulse train from the first laser source.

5. The system of claim 1, wherein the first laser pulses are configured to perform a first treatment on the stone, the second laser pulses are configured to perform a second treatment on the stone, and the combined laser pulse train is configured to shatter the stone.

6. The system of claim 1, wherein the first laser pulses are configured to heat or crack the stone, and the second laser pulses are configured to pulverize the stone.

7. The system of claim 1, wherein each of the first and second laser pulse trains have a pulse repetition rate in the range of 1 kHz to 2 GHz.

8. The system of claim 1, wherein the combined laser pulse train has a pulse repetition rate greater than a pulse repetition rate of each of the first and second laser pulse trains.

9. A system comprising:
a laser generator including a first laser source, a second laser source, and one or more shutter mechanisms configured to generate a laser energy based on a laser energy setting, the laser energy including a combined laser pulse train of first laser pulses from the first laser source and second laser pulses from the second source at a resultant pulse repetition rate;
a laser probe configured to discharge the laser energy toward a kidney or bladder stone;
a stone analyzer configured to receive a portion of the laser energy reflected from the stone, and generate an output relating to a characteristic of the stone, the characteristic including a natural or resonance frequency of the stone; and
a controller comprising at least one processor configured to receive the output generated by the stone analyzer, and determine the laser energy setting by matching the resultant pulse repetition rate of the combined laser pulse train with the natural or resonance frequency of the stone.

10. The system of claim 9, wherein the laser energy setting includes one or more settings selected from the group consisting of: a pulse width of the first or second laser pulses; a pulse repetition rate of the first or second laser pulses; a power of the first or second laser pulses; a wavelength of the first or second laser pulses; and a duration of the combined laser pulse train.

11. The system of claim 9, wherein the characteristic is selected from the group consisting of an estimated size of the stone, an estimated length of the stone, an estimated composition of the stone, and a vibration frequency of the stone.

12. The system of claim 9, further comprising memory comprising a mapping of laser energy settings to values of the output, wherein the controller controls the laser generator based on the laser energy settings of the mapping corresponding to the output.

13. The system of claim 12, wherein:
the stone analyzer comprises a laser induced breakdown spectrometer configured to (i) receive the portion of the laser energy reflected from the stone, and (ii) output a spectrometer reading indicative of a composition of the stone; and
the controller is configured to determine the laser energy setting based on the spectrometer reading.

14. A method comprising:
generating, with a first shutter mechanism, a first laser pulse train comprising first laser pulses using a first laser source;
generating, with a second shutter mechanism, a second laser pulse train comprising second laser pulses using a second laser source;
combining, with a beam combiner, based on a laser energy setting, the first and second laser pulse trains into a combined laser pulse train comprising the first and second laser pulses at a resultant pulse repetition rate;
exposing a kidney or bladder stone to the combined laser pulse train using a laser probe;
receiving, at a stone analyzer, a portion of the combined laser pulse train reflected from the stone;
generating, with the stone analyzer, an output relating to a characteristic of the stone, the characteristic including a natural or resonance frequency of the stone;
receiving, with at least one processor, the output generated by the stone analyzer; and
determining, with the at least one processor, the laser energy setting by matching the resultant pulse repetition rate of the combined laser pulse train with the natural or resonance frequency of the stone.

15. The method of claim 14, wherein combining the first and second laser pulse trains comprises temporally offsetting the first laser pulses from the second laser pulses.

16. A method comprising:
receiving, at a stone analyzer, a laser energy reflected from a kidney or bladder stone;
generating, with the stone analyzer, an output relating to a characteristic of the stone, the characteristic including a natural or resonance frequency of the stone;
determining, with a processor, a laser energy setting by matching a resultant pulse repetition rate of a combined laser pulse train with the natural or resonance frequency of the stone;
generating based on the laser energy setting, with a laser generator comprising a first laser source, a second laser source, and one or more shutter mechanisms, the combined laser pulse train to include first laser pulses from the first laser source and second laser pulses from the second source at the resultant pulse repetition rate; and
exposing the stone to the combined laser pulse train using a laser probe.

17. The method of claim 16, wherein the laser energy setting includes one or more settings selected from the group consisting of a pulse width of the first or second laser pulses, a pulse repetition rate of the first or second laser pulses, a power of the first or second laser pulses, a wavelength of the first or second laser pulses, and a duration of the combined laser pulse train.

18. A method comprising:
generating a laser energy using a laser generator including a first laser source, a second laser source, and one or more shutter mechanisms configured to produce the laser energy based on a laser energy setting, the laser energy including a combined laser pulse train of first laser pulses from the first laser source and second laser pulses from the second source at a resultant pulse repetition rate;
exposing a kidney or bladder stone to the combined laser pulse train;
receiving, at a stone analyzer, a portion of the laser energy reflected from the stone;
generating, with the stone analyzer, an output relating to a characteristic of the stone, the characteristic including a natural or resonance frequency of the stone;
receiving, with at least one processor, the output generated by the stone analyzer; and
determining, with the at least one processor, the laser energy setting by matching the resultant pulse repetition rate of the combined laser pulse train with the natural or resonance frequency of the stone,
wherein the laser energy setting includes a first power level of the first laser pulses and a second power level of the second laser pulses.

19. The method of claim 18, further comprising adjusting the laser energy setting so that the second power level is higher than the first power level, and re-exposing the stone to the combined laser train.

20. The method of claim 19, further comprising fragmenting the stone in response to the re-exposing step.

* * * * *